United States Patent [19]

Tyson

[11] 4,125,605
[45] Nov. 14, 1978

[54] METHOD OF EMPLOYING ORAL TRH

[75] Inventor: John E. Tyson, Reisterstown, Md.

[73] Assignee: The United States Government, Washington, D.C.

[21] Appl. No.: 843,367

[22] Filed: Oct. 19, 1977

[51] Int. Cl.² ..................... A61K 37/00; C07C 103/52
[52] U.S. Cl. ........................... 424/177; 260/112.5 TR
[58] Field of Search ............... 260/112.5 TR; 424/177

[56] References Cited

U.S. PATENT DOCUMENTS

| | | | |
|---|---|---|---|
| 3,860,570 | 1/1975 | Thomas et al. | 260/112.5 TR |
| 3,931,139 | 1/1976 | Wissmann et al. | 260/112.5 TR |

OTHER PUBLICATIONS

Tyson et al., J. Clin. Endocrinol Metal 40, 764 (1975).
A. Zarate et al., J. Clin. Endocrinal Metal 43, 301 (1976).
Science 116, pp. 897–900.

Primary Examiner—Delbert R. Phillips
Attorney, Agent, or Firm—Holman & Stern

[57] ABSTRACT

Improved methods of employing TRH to enhance lactation and to prolong postpartum infertility are disclosed. The methods may be employed with women following full term delivery, as well as in cases of premature birth. In addition, a method for the use of TRH in surrogate mothers is disclosed.

3 Claims, No Drawings

METHOD OF EMPLOYING ORAL TRH

BACKGROUND AND SUMMARY OF THE INVENTION

The present invention is related to a method of employing oral TRH (thyrotropin releasing hormone) in order to enhance lactation and to provide for a prolongation of postpartum infertility. More particularly, the present invention is concerned with the specific dosages, the route and timing of administration of oral TRH in order to provide such effects.

Previous methods for the administration of TRH intravenously are described, for example, by J. E. Tyson et al., *Science,* 177:897 (1972); J. E. Tyson et al., *Am. J. Obstet. Gynecol.,* 116:377 (1973); and J. E. Tyson et al., *J. Clin. Endocrinol. Metab.,* 40:764 (1975), all of which descriptions are incorporated herein by reference. The use of oral TRH is described by A. Zarate et al., *J. Clin. Endocrinol. Metab.,* 43:301 (1976). However, in this latter publication, also incorporated by reference, in which TRH was reported as administered in 20 mg. dosage capsules at intervals of three times a day, the authors concluded that TRH administered orally had no significant effect on the yield or composition of milk.

By the present invention, there is provided an improved method for orally administering TRH in order to enhance lactation and to provide for a prolongation of postpartum infertility. Advantageous results have been obtained in nursing women following full term delivery, as well as in women whose child has been born prematurely. In addition, beneficial results have been obtained in surrogate mothers by a method of treatment in which oral TRH is administered in conjunction with estrogens.

It has been found that women have enjoyed a natural state of infertility for varying periods of time depending upon the duration, frequency and intensity of nipple stimulation. Nipple stimulation has traditionally only occured in women who have wished to breastfeed their infants and indeed, there is evidence in the scientific literature to suggest that women who practice uninterrupted breastfeeding will experience an inability to ovulate for upwards of 24 months following the delivery of their child.

At the same time, however, there is evidence that a 7% incidence of pregnancy can occur in women who "breastfeed". Scientific evidence indicates that the single most important factor in determining the ability of a women to ovulate in the postpartum period is the level of her peripheral prolactin. This level is in turn determined by the frequency, intensity and duration of the nursing stimulus. Since it is impossible to calibrate the nursing interval for all women, it is possible, therefore, to enhance the secretion of prolactin by the use of certain substances. The least noxious of these substances has proven to be thyrotropin releasing hormone (TRH).

The present invention is unique in that it utilizes a well known physiologic fact, namely, that prolactin secretion in women postpartum is significantly elevated and is associated with the enlargement of the prolactin-secreting cells. These cells are at the same time more sensitive to stimulation from very low doses of TRH. Since TRH is also known to release thryotropin, it is of some concern that an additional effect of TRH might be seen on maternal thyroid physiology. This effect, however, has never been seen since the does of TRH necessary to produce a maximum prolactin response is 5 to 10 times lower than that dose required to produce a threshold response from the pituitary gland in terms of thyrotropin secretion. Thus, the use of TRH in postpartum women in low doses is very effective in 95% of instances in elevating the peripheral prolactin concentration.

It has been found that all women who breastfeed effectively must have a basal plasma prolactin concentration in excess of 30 nanograms per milliliter. More than 80% of women who breastfeed have such a level. However, for reasons of decreased frequency of nursing brought about by supplementation of the infants's diet with exogenous food, the prolactin concentration may actually fall below 30 nanograms per milliliter. If this persists for more than 2-3 days, even though a mother may be willing to breastfeed her child, milk production is decreased. At the same time, the decrease in the prolactin level brought about by the decreased frequency of feeding will be associated with a resumption in the secretion of pituitary gonadotropins—those hormones necessary for stimulation of ovarian function.

In accordance with the present invention, it has been found that the administration of 5-10 milligrams of oral TRH, twice a day at intervals of about 12 hours for about 5 days to women whose plasma prolactin falls below 30 ng/ml is associated with an increase secretion of prolactin by the woman and a resumption of milk production with a subsequent increase in milk volume. It has been further shown that suckling-stimulated prolactin release is also enhanced in women taking this dose of TRH twice a day and this in turn increases the production of milk endogenously.

It is thus seen, in accordance with the present invention, that a five day course of oral TRH 5-10 mg twice a day will be associated with an increase in the peripheral plasma prolactin concentration increasing the milk production by the mother and making more milk available to the infant. At the same time, this dose of TRH will provoke an increased prolactin response to the sucking efforts of the child and therefore increse milk production by that woman. The present data suggests that in the dosage levels mentioned, there is little or no effect of TRH on thyroid function in such women, yet the increased secretion of prolactin will further impair fertility by interfering with gonadotropin secretion at the pituitary gland.

Approximately 20% of women, for one reason for another, have difficulty with breastfeeding. Part of this is due to fear of the procedure and part due to an inability of the child to stimulate the nipple adequately due, often, to abnormalities of the lip and the palet of the child. It is to be conceded that breastfeeding in such infants is advantageous and therefore should be supported in any way possible.

A second group of infants that will benefit tremendously from breastfeeding are those born prematurely. Previously, it had not been deemed possible for mothers of premature infants to breastfeed because of a failure of lactation to be initiated. This failure is thought to be due to inadequate preparation of the pituitary gland for the secretion of prolactin. Yet, it has been found in accordance with the present invention that the pituitary prolactin cells can be stimulated to secrete prolactin through the oral administration of TRH. Thus, an additional use of TRH would be in a dose of 10 mg twice a day to mothers who have delivered premature infants. This dosage would elevate the prolactin concentration and would increase the likelihood of the initiation of lactation. It is suggested from present research that such therapy be administered to these women until the maternal mammary milk volume exceeds 300 ml a day. Often, this is easily measurable since the mother is pumping the breast in order to give the milk to the child by some artificial means. The successful use of TRH in such women is predicated on the administration of the first dose of TRH within the first 12 postpartum hours and every 12 hours thereafter for approximately 5–10 days.

An additional use of TRH is in surrogate mothers. Studies in accordance with the present invention have involved the administration of TRH to adoptive mothers. In most instances, such women have undergone voluntary sterilization following the birth of natural children but, for one reason or another, wish to have another child. By the present invention, lactation has been induced in such women for the benefit of their adopted child by attempting to simulate the effects of pregnancy on prolactin secretion and, at the same time, by requesting that the mother practice auto-stimulation of the nipple. The technique of stimulation is as follows: Women are treated with 5 to 10 mg of conjugated estrogens equine twice a day for 14 days. Caution with regard to the possibility of side effects is given to each woman based upon the known effects of such estrogens on the vascular system. Beginning on the 7th day of estrogen treatment, oral TRH 5–10 mg twice a day, at intervals of about 12 hours, is administered for the final 7 days of treatment with estrogen. At the end of the 14th estrogen-treatment day, TRH is continued while the frequency of nipple stimulation is increased from four times daily to every 4 hours. In the women studied thus far, milk production can be induced within 72 hours following the withdrawal of the estrogen. Associated with this is an increase in the basal plasma prolactin concentration. Milk production thereafter varies depending upon the willingness of the adopted child to take the breast. It has also been found that induction of lactation is much easier in women who have previously had children although the series of women studied who have adopted children but have never been pregnant themselves is too small to draw any final conclusions The administration of TRH may also be initiated in puerperally lactating mothers who have to undergo emergency surgery such as polycystectomy, apendectomy, or the repair of fractures. Such surgery usually takes the mother away from the child for periods of time up to 14 days and a mother who is desirous of breastfeeding may find great difficulty in reestablishing lactation when she returns home from the hospital. In such cases, the administration of TRH has been associated with the reestablishment of lactation within 48 hours. It is to be emphasized that such lactation cannot be firmly established without coincident sucking of the nipple by the child.

DESCRIPTION OF THE PREFERRED EMBODIMENTS

In accordance with the present invention, the effect of oral TRH has been evaluated on the secretion of prolactin (PRL) and on maternal mammary function. The tripeptide was administered to puerperal women practicing full or partial nursing, and the effect was monitored in mothers and infants through the measurement of the plasma concentrations of PRL, gonadotropins, GH, TSH, $T_4$ and milk composition.

The results support the hypothesis that TRH is effective in releasing endogenous PRL. Furthermore, such release is not necessarily associated with objective signs of increased milk production of breast engorgement unless the woman practices partial nursing either voluntarily or as a result of lactational insufficiency. The data also imply that precautions should be observed regarding the does of TRH administered to nursing mothers so as to avoid the risk of iatrogenic hyperthyroidism.

Since previous definitions of full and partial nursing vary widely, the following definitions have been employed. Full nursing represents a regular schedule of breastfeeding of at least six nursing events per day where the total nutritional requirement of the infant is obtained from maternal suckling. Supplementation is limited to water. Partial nursing is a schedule of three or four nursing intervals per day where supplemental feeding of synthetic milks, juices, or other liquid nutrients are provided. This may be further subdivided according to the time postpartum. Partial nursing prior to the 90th postpartum day may be involuntary due to an inadequate production of milk (lactational insufficiency). Partial nursing beyond the 90th postpartum day may result from increasing infant nutritional demands which exceed maternal mammary capacity.

Healthy, non-obese mothers between 16–34 years of age volunteered to participate predicated on the completion of a normal, full-term vaginal delivery. A thorough verbal explanation of the objectives of this project were presented to each volunteer by a physician and a nurse-midwife after which written informed consent was obtained. The study was approved by the Joint Committee on Clinical Investigation of the Johns Hopkins University School of Medicine and the Johns Hopkins School of Hygiene and Public Health, The Catholic University of Chile, and the University of Chile. TRH used in these studies was a crystalline powder admixed with lactose sugar and sealed in a soft gelatin capsule, prepared according to methods well known in the art. Other pharmaceutically acceptable carriers, fillers, flavoring and sweetening agents and other therapeutically inert ingredients may also be employed along with TRH in making up the dosage composition, according to methods well known in the art.

EXAMPLE I

To test the efficacy of TRH, six nursing women between the 5th and 35 postpartum days were studied. Each received one 5 mg capsule of TRH in the early morning after an overnight fast. Six nursing women matched for postpartum interval received a placebo of lactose sugar. Blood samples were drawn from an indwelling catheter in an antecubital vein at −5,0,30,60,120, and 180 min.

EXAMPLE II

Sixty women volunteered for this major study and each was instructed to practice full nursing for at least 90 postpartum days. Fifty percent of the women were dropped from the study before the end of the first postpartum month due to changes in nursing patterns. The remaining 30 women were randomly divided into TRH and control groups. Group homogeneity is shown in Table 1. TRH, 5 mg or a lactose placebo, was administered daily at 0800 and 2000 h for 30 days beginning on day 29 postpartum. Blood and milk samples were obtained on the first postpartum day and at weekly intervals between 1500 and 1600 h. Thus, blood samples were never obtained sooner than 7 h after the ingestion of TRH. Each women's nursing pattern was recorded by nurse-midwives. Charts of infant growth and development were plotted weekly.

TABLE 1

Data for control and TRH-administered patients

| | Mean age (years) | Mean maternal weight (kg) | Nursing duration (min) | Nursing frequency per day | Mean infant birth weight (gm) |
|---|---|---|---|---|---|
| Control (15)* | 22.3 | 53.4 | 27.7 | 6.6 | 3,329 |
| TRH (15) | 26.3** | 56.3 | 25.7 | 5.8 | 3.323 |

* Number of patients.
** There is no significant difference between the groups for any of the parameters.

EXAMPLE III

A group of 13 women with lactational insufficiency practicing partial nursing between 13-71 postpartum days were next studied. Four received TRH 5 mg and nine received 20 mg twice a day at 0800 and 2000 h for 5 days. Blood samples were obtained prior to the first capsule and daily thereafter for 5 days before taking the morning dose of TRH. Daily milk samples were also collected.

With regard to sampling procedures, individual blood samples were collected in heparinized vacuum tubes. Neither nursing nor maternal food intake had occurred in the previous 3 h. The sampling procedure in Examples II and III consisted of placing the patient at rest for a minimum of 15 min after which blood was drawn from an antecubital vein. Blood samples were centrifuged and plasma was removed and stored at −20C. Samples originating outside the continental United States were delivered to the laboratory at quarterly intervals in dry ice by special messenger.

In Examples II and III, milk was obtained from each breast following blood sampling and immediately prior to nursing. The women were instructed to grasp first the right and then the left breast, kneading it gently toward the nipple. Thus, 10 ml or more of the fore milk was removed with ease through each nipple and combined in a sterile container. The sample was thoroughly mixed by vigorous shaking. A compressed tablet of mercuric chloride and potassium dichromate was then added as a preservative to each sample before storing.

Assay Methods

A set of specific radioimmunoassays were employed for the measurement of plasma hormones. PRL was measured by a modification of the radioimmunoassay of Hwang et al., *Proc. Nat. Acad. Sci.*, 68:1902 (1971) using the iodination technique of Greenwood et al., *Biochem J.*, 89:114 (1963). Plasma LH and FSH were measured by using a modification of the double antibody radioimmunoassay of Midgely, *Endocrinology*, 79:10 (1966). Thyrotropin (TSH) was determined by a double antibody radioimmunoassay of Odell, Rayford and Ross, *J. Lab. Clin. Med.*, 70:973 (1967). Plasma thyroxine ($T_4$) by column was measured by the method of Pileggi and Kessler, *Clin. Chem.*, 14:339 (1968). A modification of the immunoassay of Roth et al., *Science*, 140:987 (1963), was used to measure plasma growth hormone (GH) utilizing the iodination technique for prolactin. Antibody bound radioactivity was separated by the dextran-charcoal method of Herbert et al., *J. Clin. Endocrinol. Metab.*, 25:1375 (1965). Each of the references mentioned in this paragraph is incorporated herein by reference.

For the analysis of milk composition, samples were thawed and held at room temperature for no more than 30 min. Aliquots were analyzed for percent fat, protein and lactose concentrations using the infrared milk analyzer (IRMA). Samples less than 30 ml in volume (about 10% of the total) were diluted up to 35 ml with distilled water. These were then homogenized with a Biosonic Model 3 Ultrasonicater (Bronwill Scientific Co., Rochester, N.Y.) at an exposed intensity of 70 vibrations per second for 30 sec. These samples were stored overnight at 4° C. and then analyzed for composition. Corrections were made for any dilution.

RESULTS

EXAMPLE I

Initally, the efficacy of oral TRH in stimulating PRL secretion was evaluated in six nursing mothers. Following the administration of 5 mg TRH, a mean maximal PRL increment of 46.3 ng/ml was observed at 60 min. Peripheral PRL remained elevated throughout the sampling period. The wide SEM reflects the range of baseline PRL levels at varying postpartum intervals. Six women receiving a placebo showed no increment in PRL.

Plasma TSH remained unchanged in control women. However, mean plasma TSH in TRH-treated women rose from $2.6 \pm 0.3$ $\mu$U/ml at 0 time to $11.4 \pm 2.9$ $\mu$U/ml at 60 min and $17.6 \pm 5.2$ $\mu$U/ml at 180 min. Plasma $T_4$ determinations before and 24 h following each test were within the normal range (2.9 to 6.4 mcg/dl) and did not rise.

EXAMPLE II

During treatment with 5 mg TRH twice daily, maternal weight similar to that of controls. Likewise, the growth charts of infants of TRH-treated mothers were similar to those of control infants. The mean increment in weekly infant weight was similar in infants of both control and TRH mothers. Repeated evaluations at 12 and 16 weeks implied no difference in the weight gain of infants whose mothers had received the oral tripeptide TRH. The data would also seem to support breastfeeding as an ideal source of infant nutrition since the comparison of the mean weights of these infants with a group of infants of bottle feeding mothers showed a significantly lower increment of growth among the bottle feeders. Weekly records of maternal and infant temperature, pulse, respirations, and blood pressure in infants of TRH-treated mothers were comparable to the results obtained in controls.

Both maternal and infant thyroid status were evaluated by measuring plasma TSH and $T_4$. Plasma TSH at 5 and 9 weeks postpartum were $2.6 \pm 0.1$ and $2.8 \pm 0.2$ $\mu$U/ml in control mothers compared to $2.9 \pm 0.2$ and $2.3 \pm 0.2$ $\mu$U/ml in oral TRH-treated mothers. TSH values in the infants of controls were 4.0 and 2.8 $\mu$U/ml at the same time intervals compared to 4.2 and 3.1 $\mu$U/ml in infants of TRH-treated mothers. No significant difference was observed in these results. Although maternal plasma TSH was found to be elevated at 180 min following TRH ingestion, no prolonged effect on plasma TSH was observed nor was there any effect on plasma TSH concentrations in the infants of TRH-treated mothers. $T_4$ values were also normal and remained normal throughout the study period.

The administration of TRH was not associated with any significant change in the weekly 1500 h maternal PRL concentration. Likewise, milk composition in terms of the percent of fat and protein concentration did not differ significantly between the TRH and control groups. However, a gradual and significant decline in the mean percent milk protein concentration was observed in both groups between the first and the 12th postpartum weeks ($P<0.02$). Table 2 presents the plasma GH and PRL concentrations in infants of TRH and control mothers. Physiologic elevations in the peripheral concentration of the two pituitary polypeptides were evident in both groups and unrelated to treatment. The differences could also be related to the small sample size.

TABLE 2

Infant plasma growth hormone and prolactin concentrations before and after the use of oral TRH or placebo in the mother

|  |  | Week 1 | Week 5 | Week 9 |
|---|---|---|---|---|
| Growth hormone (ng/ml) | Placebo | 43.4±4.9* (9)** | 12.5±2.9 (13) | 4.3±1.1 (6) |
|  | Oral TRH*** | 32.2±4.9 (11) | 8.8±2.1 (11) | 8.6±2.2 (11) |
| Prolactin (ng/ml) | Placebo | 198.0±23.6 (9) | 35.6±6.2 (13) | 14.3±2.2 (6) |
|  | Oral TRH | 200.3±19.2 (15) | 31.5±3.8 (15) | 23.1±4.2 (15) |

* Mean ± SE
** Number of infants sampled
*** Using a two tailed Student's t test, there was no significant difference between the placebo and TRH groups at any week A period of natural infertility usually accompanies puerperal nursing. Only one woman experienced vaginal bleeding during the 90 day study period. An endometrial biopsy on the first day of bleeding produced proliferative phase endometrium reflecting estrogenization. Gonadotropin concentrations were measured weekly in all women. Due to cross reactivity with chorionic gonadotropin (hCG), LH could not be measured in the first 24 h postpartum. Changes in LH were less dramatic. Gonadotropin levels were identical in controls. Beyond the 14th postpartum week when many women began partial nursing, postovulatory vaginal bleeding was recorded, but no difference in bleeding patterns between TRH-treated and placebo-treated mothers could be identified.

EXAMPLE III

The failure to observe changes in maternal milk composition following the ingestion of oral TRH in Example II may have been related to the practice of full nursing. It was decided that TRH should be evaluated in women who wished to practice full nursing but, for unknown reasons (not nutritional), were partially nursing.

In the four who received 5 mg of TRH every 12 h for 5 days, a consistent 50% increase was observed in the PRL concentration. Milk production and letdown were increased. For the nine women who received 20 mg of TRH twice daily, mean plasma PRL levels and milk compositions are shown in Table 3. In three instances, the pretreatment basal PRL was more than two SD below the mean basal PRL derived for a large group of normal women previously reported from this laboratory. Nevertheless, the morning basal PRL value on days two and three of therapy was significantly elevated. The mean percent fat composition of milk on day two of treatment was almost 1% greater than that seen during pretreatment, yet the difference was not significant. Conversely, a slight fall in the percent of protein composition was observed during TRH administration. The percent of lactose concentration remained constant in the milk samples obtained from all studies. As a result of TRH ingestion, each women reported subjective and objective increases in breast engorgement and milk letdown and all were able to return to full nursing.

As an experimental exercise, two women with insufficient lactation gave consent for the administration of 40 mg of oral TRH twice a day or the same time schedule as noted above. On the 7th day of therapy the patients were reevaluated and found to have lost weight. Their pulse rate was elevated as was their blood pressure. A clinical diagnosis of thyrotoxicosis was made. Plasma TSH was 23 $\mu$U/Ml and 44.2 $\mu$U/ml respectively. Plasma $T_4$ was 10.4 mcg/dl and 11.6 mcg/dl. The medication was discontinued on the basis of clinical symptoms and the patients were reevaluated within 10 days at which time no clinical or laboratory evidence of hyperthyroidism was observed. It is not known whether these clinical manifestations were a mere chance finding since the first woman was Chilean while the second was treated in Baltimore.

TABLE 3

Plasma prolactin and milk composition before and during the ingestion of 20 mg oral TRH twice daily in nine partially nursing women between day 13-71 postpartum

|  |  | Day |  |  |  |  |
|---|---|---|---|---|---|---|
|  |  | 1 | 2 | 3 | 4 | 5 |
| Plasma PRL (ng/ml) | Mean ± SE | 27.8±5.3 | 53.1±8.7 | 73.3±12.4 | 44.1±7.0 | 54.8±13.9 |
|  | P value* |  | .0005 | .005 | NS | NS |
| % Milk fat | Mean ± SE | 2.99±0.4 | 3.88±0.6 | 3.21± 0.4 | 3.79±0.4 | 3.02±0.2 |
|  | P value |  | NS | NS | NS | NS |
| % Milk protein | Mean ± SE | 1.81±0.2 | 1.63±0.2 | 1.61± 0.1 | 1.62±0.1 | 1.60±0.1 |
|  | P value |  | NS | NS | NS | NS |

*As compared to day 1 (before initial ingestion of oral TRH)

Specific regulation of PRL secretion in the immediate puerperium is poorly understood, yet is is known that peripheral PRL levels rise in response to suckling. Furthermore, the selective inhibition of PRL secretion in the immediate puerperium is followed by a failure to lactate. Stimulation of PRL secretion in nursing mothers by iv TRH is followed by alterations in mammary milk production suggesting that PRL is necessary for the initiation and maintenance of human lactation. On the other hand, high levels of PRL influence the composition of human milk since, as basal PRL levels fall in the first 60-90 postpartum days, so does the percent of fat composition of human milk. Basal PRL concentrations in our nursing mothers were significantly higher than those of nonnursing mothers even though both sets of values lie within the range of normal for pre-pregnant women, confirming the work of others. Whether PRL plays an active or a permissive role in continued lactation is unknown. It seemed reasonable, therefore, to evaluate the ability of a specific PRL secretogogue, TRH, to stimulate PRL release and to evaluate this release on mammary milk production. Rabello and associates having shown that high doses of oral TRH could provoke lactation in normally menstruating women, as described at *J. Clin. Endocrinol.* 39, 574 (1974).

For the present study, a low dose of TRH was ideal in that both prolactin and TSH secretion were stimulated acutely. However, there was no significant long term effect on circulating levels of either hormone. While the ingestion of as little as 5 mg of TRH was associated with a signifcant increment in TSH, there was no change in basal thyroxine. It is conceivable that subtle changes in peripheral thyroxine concentrations did occur, but were missed due to the sampling interval. On the other hand, no changes in basal TSH concentrations were observed beyond the time of maximal TRH effect; that is 24 h later. Higher dose of TRH provoke excessive TSH secretion and subsequent thyroid stimulation. This was noted in two puerperal women in partial lactation who volunteered to ingest 40 mg twice daily for 1 week. Although similar doses have been administered to menstruating women without demonstrable side effects, this risk remains. It may be that the puerperal thyroid gland is more sensitive to TSH.

While the dosage regimen of TRH was limited to every 12, h, it has been concluded that a significant increment in PRL could be expected to follow each dose as shown in the acute experiments. This increment might therefore influence subsequent mammary milk production. Unfortunately, this was not seen in women practicing full nursing, which may be related to the presence of an already maximal mammary response to repeated suckling. Conversely, the ingestion of TRH by women in partial lactation produced in increase in breast engorgement and milk letdown and a significant increase in the basal PRL concentration on the first 2 days of oral TRH ingestion.

Previously, there has been reported a variable, sometimes significant rise in the percent of maternal milk fat and protein composition following the iv administration of TRH. No such changes were found with the dosages of oral TRH used in this study. In fact, both groups showed a decline in the mean percent of protein concentration in samples obtained at weekly intervals for 3 months. Such changes may subsequently be shown to correlate with the basal PRL concentration.

Studies of human lactation are limited by the relative inaccessibility of the total milk volume for examination. Alterations in mammary milk production occur at an individual feeding and are influenced by the duration, frequency, and intensity of nursing. For this reason, the first sample of milk was obtained for compositional analysis before the child was allowed to suck, standardizing this against the time of day. Further control on nursing in same study population were made based upon the time of the last feeding and the time of maternal food ingestion-known determinants in the composition of human milk.

The absence of the slightest difference between the infant weights of mothers receiving TRH and those receiving placebo suggests that infant nutrition was not acutely influenced by the study. While some investigators have suggsted using post-nursing infant weights as an index of mammary milk production, this method has been unsatisfactory since one major limiting factor to this measurement is the volume of the infant's stomach.

For puerperal women in whom lactation is desirable, such as those who must cease lactation for an interval operative procedure or an infection, the use of TRH might promote a resumption of mammary milk production and letdown at a later date. Of equal importance is the recent finding that elevated PRL concentrations might influence corpus luteum function. Under these circumstances, oral TRH through its ability to release PRL, may be an important adjunct in the maintenance of puerperal lactation and the prolongation of puerperal infertility.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

The embodiments of the invention in which an exclusive property or privilege is claimed are defined as follows:

1. In a method for enhancing lactation in a postpartum woman, the improvement which comprises orally administering to said woman from 5 to 10 mg of TRH twice a day at about 12 hour intervals for a period of approximately 5 days.

2. In a method for enhancing lactation in a postpartum woman following delivery of a child born prematurely, the improvement which comprises orally administering to said woman about 10 mg of TRH twice a day at about 12 hour intervals for approximately 5 to 10 days.

3. In a method for inducing lactation in a woman, the improvement which comprises:
  (a) treating the woman with from 5 to 10 mg of conjugated estrogens equine twice a day at about 12 hour intervals for about 14 days;
  (b) orally administering to the woman from 5 to 10 mg of TRH twice a day at about 12 hour intervals during the final 7 days of treatment with estrogens:
  (c) stimulating the nipples of the woman 4 times daily at intervals of about 6 hours during the 14 day treatment with estrogens;
  (d) orally administering to the woman from 5 to 10 mg of TRH twice a day at intervals of 12 hours for about 3 days following the 14 day estrogen treatment; and
  (e) stimulating the nipples of the woman 6 times daily at intervals of about 4 hours during the 3 day period of step (d).

* * * * *